US009834792B2

(12) United States Patent
Trevethick et al.

(10) Patent No.: US 9,834,792 B2
(45) Date of Patent: Dec. 5, 2017

(54) MULTI-STAGE BIOREACTOR PROCESSES

(71) Applicant: LanzaTech New Zealand Limited, Skokie, IL (US)

(72) Inventors: Simon Richard Trevethick, Skokie, IL (US); Jason Carl Bromley, Skokie, IL (US); Guy William Waters, Skokie, IL (US); Michael Koepke, Skokie, IL (US); Loan Phuong Tran, Skokie, IL (US); Rasmus Jensen Overgaard, Skokie, IL (US)

(73) Assignee: LANZATECH NEW ZEALAND LIMITED, Auckland (NZ)

( * ) Notice: Subject to any disclaimer, the term of this patent is extended or adjusted under 35 U.S.C. 154(b) by 20 days.

(21) Appl. No.: 14/920,862

(22) Filed: Oct. 22, 2015

(65) Prior Publication Data
US 2016/0115505 A1    Apr. 28, 2016

Related U.S. Application Data

(60) Provisional application No. 62/067,379, filed on Oct. 22, 2014, provisional application No. 62/067,405, filed on Oct. 22, 2014.

(51) Int. Cl.
*C12M 1/04* (2006.01)
*C12P 7/14* (2006.01)
*C12M 1/00* (2006.01)

(52) U.S. Cl.
CPC .............. *C12P 7/14* (2013.01); *C12M 23/58* (2013.01); *C12M 29/18* (2013.01); *Y02E 50/17* (2013.01)

(58) Field of Classification Search
None
See application file for complete search history.

(56) References Cited

U.S. PATENT DOCUMENTS

| 5,173,429 A | 12/1992 | Gaddy et al. |
| 5,593,886 A | 1/1997 | Gaddy |

(Continued)

FOREIGN PATENT DOCUMENTS

| EP | 117309 A1 | 9/1984 |
| WO | 199800558 A1 | 1/1998 |

(Continued)

OTHER PUBLICATIONS

Abrini, J. Naveau, H. & Nyns, E. J., Archives of Microbiology, (1994), 161, 345-351.

(Continued)

*Primary Examiner* — Robert Yamasaki
*Assistant Examiner* — Charles Zoltan Constantine
(74) *Attorney, Agent, or Firm* — Frank S Molinaro

(57) ABSTRACT

Multi-stage, biological processes and systems for converting a C1 carbon source to desired end products are described. The processes comprise dividing a gaseous C1-containing substrate, in parallel, among multiple bioreactor stages. Liquid products are successively fed, in series, from a first bioreactor stage to downstream bioreactor stages. Operation can be simplified by avoiding the requirement for microorganism separation and recycle at each stage. In addition, overall vapor-liquid mass transfer for the combined stages is very favorable, leading to high end product productivity with comparably low byproduct metabolite productivity.

24 Claims, 5 Drawing Sheets

(56) References Cited

U.S. PATENT DOCUMENTS

| | | | |
|---|---|---|---|
| 6,368,819 B1 | 4/2002 | Gaddy et al. | |
| 2005/0064577 A1* | 3/2005 | Berzin | B01D 53/85 435/266 |
| 2011/0212433 A1 | 9/2011 | Barker et al. | |
| 2014/0080117 A1* | 3/2014 | Snyder | G01N 21/31 435/3 |
| 2014/0273125 A1* | 9/2014 | Hickey | C12P 7/16 435/160 |

FOREIGN PATENT DOCUMENTS

| WO | 200068407 A1 | 11/2000 |
|---|---|---|
| WO | 200208438 A2 | 1/2002 |
| WO | 2007117157 A1 | 10/2007 |
| WO | 2008028055 A1 | 3/2008 |
| WO | 2008115080 A1 | 9/2008 |
| WO | 2009022925 A1 | 2/2009 |
| WO | 2009064200 A2 | 5/2009 |
| WO | 2009151342 A1 | 12/2009 |
| WO | 2010093262 A1 | 8/2010 |
| WO | 2011002318 A1 | 1/2011 |
| WO | 2011112103 A1 | 9/2011 |
| WO | 2012024522 A1 | 2/2012 |
| WO | 2012026833 A1 | 3/2012 |
| WO | 2012053905 A1 | 4/2012 |
| WO | 2012115527 A1 | 8/2012 |
| WO | 2013036147 A2 | 3/2013 |
| WO | 2013180581 A1 | 12/2013 |
| WO | 2013180584 A1 | 12/2013 |
| WO | 2013185123 A1 | 12/2013 |
| WO | 2013191567 A1 | 12/2013 |
| WO | 2014036152 A1 | 3/2014 |

OTHER PUBLICATIONS

Ragsdale, Stephen W. et al., Acetogenesis and the Wood-Ljungdahl Pathway of CO2 Fixation, Biochim Biophys Acta, (2008), 1873-1898, 1784(12).

Drake Harold L. et al., Acetogenic Prokaryotes, Prokaryotes, (2006), 2:354-420, 3rd edition, New York, NY.

Tanner, Ralph S. et al., *Clostridium ljungdahlii* sp. nov., an Acetogenic Species in Clostridial rRNA Homology Group I, International Journal of Systematic Bacteriology, (1993), 232-236.

Perez, Jose M. et al., Biocatalytic reduction of short-chain carboxylic acids into their corresponding alcohols with syngas fermentation, Biotechnology and Bioengineering, (2012), 110, 1066-1077.

Koepke, Michael et al, Fermentative production of ethanol from carbon monoxide, Current Opinion in Biotechnology, (2011), 22, 320-325.

Tirado-Acevedo O., Production of Bioethanol from Synthesis Gas Using Clostridium ljungdahlii. PhD thesis, North Carolina State University, 2010.

* cited by examiner

MULTI-STAGE BIOREACTOR PROCESSES

FIELD OF THE INVENTION

Aspects of the invention relate to processes for the microbial fermentation of a C1-containing substrate to end products, utilizing multiple bioreactor stages. In representative processes, the C1-containing substrate is divided among the stages for gas phase processing in parallel, whereas liquid products are passed from one stage to the next, successive stage for liquid phase processing in series.

DESCRIPTION OF RELATED ART

Environmental concerns over fossil fuel greenhouse gas (GHG) emissions have led to an increasing emphasis on renewable energy sources. As a result, ethanol is rapidly becoming a major hydrogen-rich liquid transport fuel around the world. Continued growth in the global market for the fuel ethanol industry is expected for the foreseeable future, based on increased emphasis on ethanol production in Europe, Japan, and the United States, as well as several developing nations. For example, in the United States, ethanol is used to produce E10, a 10% mixture of ethanol in gasoline. In E10 blends, the ethanol component acts as an oxygenating agent, improving the efficiency of combustion and reducing the production of air pollutants. In Brazil, ethanol satisfies approximately 30% of the transport fuel demand, as both an oxygenating agent blended in gasoline, and as a pure fuel in its own right. In addition, the European Union (EU) has mandated targets, for each of its member nations, for the consumption of sustainable transport fuels such as biomass-derived ethanol.

The vast majority of fuel ethanol is produced via traditional yeast-based fermentation processes that use crop derived carbohydrates, such as sucrose extracted from sugarcane or starch extracted from grain crops, as the main carbon source. However, the cost of these carbohydrate feed stocks is influenced by their value in the marketplace for competing uses, namely as food sources for both humans and animals. In addition, the cultivation of starch or sucrose-producing crops for ethanol production is not economically sustainable in all geographies, as this is a function of both local land values and climate. For these reasons, it is of particular interest to develop technologies to convert lower cost and/or more abundant carbon resources into fuel ethanol. In this regard, carbon monoxide (CO) is a major, energy-rich by-product of the incomplete combustion of organic materials such as coal, oil, and oil-derived products. CO-rich waste gases result from a variety of industrial processes. For example, the steel industry in Australia is reported to produce and release into the atmosphere over 500,000 metric tons of CO annually.

More recently, micro-organism (bacterial) based process alternatives for producing ethanol from CO on an industrial scale have become a subject of commercial interest and investment. The ability of micro-organism cultures to grow, with CO being the sole carbon source, was first discovered in 1903. This characteristic was later determined to reside in an organism's use of the acetyl coenzyme A (acetyl CoA) biochemical pathway of autotrophic growth (also known as the Woods-Ljungdahl pathway and the carbon monoxide dehydrogenase/acetyl CoA synthase (CODH/ACS) pathway). A large number of anaerobic organisms including carboxydotrophic, photosynthetic, methanogenic, and acetogenic organisms have since been shown to metabolize CO. Anaerobic bacteria, such as those from the genus *Clostridium*, are known to produce ethanol from CO, $CO_2$ and $H_2$ via the acetyl CoA biochemical pathway. For example, various strains of *Clostridium ljungdahlii* that produce ethanol from gases are described in WO 00/68407; EP 1117309 A1; U.S. Pat. Nos. 5,173,429; 5,593,886; 6,368,819; WO 98/00558; and WO 02/08438. The bacterium *Clostridium autoethanogenum* sp is also known to produce ethanol from gases (Abrini et al., ARCHIVES OF MICROBIOLOGY 161: 345-351 (1994)).

Because each enzyme of an organism promotes its designated biological conversion with essentially perfect selectivity, microbial synthesis routes can achieve higher yields with lower energy costs compared to conventional catalytic routes. For example, the energy requirements for separating byproducts, which result from non-selective side reactions, from the desired products may be reduced. In addition, concerns over the poisoning of catalysts, due to impurities in the reaction medium, are diminished. Despite these apparent advantages, however, the art must address certain challenges presently associated with the microbial synthesis of ethanol from CO, particularly in terms of ensuring that the production rate is competitive with other technologies. When using CO as their carbon source, the anaerobic bacteria described above produce ethanol by fermentation, but they also produce at least one metabolite, for example $CO_2$, methane, n-butanol, and/or acetic acid. The formation of any of these metabolites has the potential to significantly impact productivity and overall economic viability of a given process, as available carbon is lost to the metabolite(s) and the production efficiency of the desired end product is compromised. In addition, unless a metabolite (e.g., acetic acid) itself has value at the time and place of the microbial fermentation process, it may pose a waste disposal problem. Various proposals for addressing the formation of products other than the desired end product in the anaerobic fermentation of CO-containing gases to make ethanol are discussed in WO2007/117157, WO2008/115080 and WO2009/022925.

Ethanol production rate, which is a key determinant as to whether a given fermentation process is economically attractive, is highly dependent on managing the appropriate conditions for bacterial growth. For example, it is known from WO2010/093262 that the CO-containing substrate must be provided to a microbial culture at a rate that results in optimal microbial growth and/or desired metabolite production. If insufficient substrate is provided, microbial growth slows and the fermentation product yields shift toward acetic acid at the expense of ethanol. If excessive substrate is provided, poor microbial growth and/or cell death can result. Further information regarding the relationships among operating parameters in these processes is found in WO2011/002318.

The art of biological processes for producing ethanol from CO, and particularly CO-containing waste streams such as the gaseous effluents emitted in steel production, is continually seeking solutions that improve process economics and therefore industry competitiveness. According to conventional practice, the separation and recycle of the microorganisms that are used to carry out the desired conversion are considered essential to achieving acceptable productivity in continuous processes. Suitable membrane separation systems, either internal or external to the bioreactor, are known to be effective for this purpose. However, membranes and their associated housings, valves, instrumentation, and controls add significantly to the overall capital and operating costs. Changing membranes and "cleaning in place" (CIP) options, whether manual or automatic, generally require either a significant amount of operator time, chemicals, and heating (in the case of manual operation) or a prohibitively high capital cost (in the case of automatic operation). For example, some bioreactor systems have required expensive enzyme solutions to clean cell recycle membranes, as simple cleaning with caustic (NaOH) solution has been found ineffective in practice.

Overall, important considerations in biological CO conversion processes relate to finding improvements that increase operating flexibility, improve ethanol productivity and product quality, and/or more efficiently utilize CO. Achieving even modest advances in any one of these areas, without substantially impacting capital and operating expenses, can have significant implications on the industrial scale of operation.

SUMMARY OF THE INVENTION

Aspects of the invention relate to improvements in biological processes and associated systems for the generation of useful end products such as ethanol, generated through metabolic pathways of a C1-fixing microorganism that utilize, as a nutrient, C1 carbon source from a C1-containing substrate such as an industrial waste gas. Representative processes and systems involve alternative types of operation using multiple stages of interconnected bioreactors, and particularly operation in which it is possible to forego the expense and complexity of separating the carboxydotrophic microorganism for recycle to at least one of the stages (e.g., to at least one bioreactor of the stages), generally most of the stages (e.g., all stages except for the first stage and/or the last or final stage), and often all of the stages, used in the overall process. Surprisingly, the use of such a system, and particularly one in which a C1-containing substrate is fed in parallel to multiple bioreactors, whereas liquid products are fed in series, has been demonstrated to result in high overall ethanol productivity with correspondingly low productivity of undesired metabolites such as acetic acid. Other advantages, including efficient overall C1 carbon source utilization, as well as improved process flexibility and control, are also realized.

Embodiments of the invention are directed to multi-stage processes for converting C1 carbon source into an end product. Representative processes comprise feeding a gaseous C1-containing substrate, in parallel, to a first bioreactor stage and at least a second bioreactor stage of the process, for example by dividing the C1-containing substrate among the bioreactor stages, such that the gas composition received at each stage is the same or substantially the same and represents that of the C1-containing substrate that is input to the process. Such processes further comprise feeding at least a portion of a first stage liquid product, in series, from the first bioreactor stage to the second bioreactor stage. In this manner, the composition of the liquid product received at each stage, or at least a biomass free liquid fraction (e.g. a fraction of the liquid broth which does not contain —C1-fixing microorganism) thereof, can represent the output received from the prior, upstream stage. Therefore, the composition of the liquid product received at each stage, unlike the gas composition, is generally not the same and can in fact vary significantly with respect to concentrations of the desired end product and other metabolites. For example, the concentration of desired end product can increase progressively over at least some, and preferably all, stages, in the direction from upstream to successive downstream stages. Alternatively, or in combination, other metabolites can decrease progressively over some or all of such stages. Embodiments of the invention are directed to multi-stage processes for converting C1 carbon source from a C1-containing substrate to a desired end product, wherein the multi-stage process increases the specificity of the system to the desired end product.

In addition, the separation and recycle of the C1-fixing microorganism is advantageously avoided in at least one of the bioreactor stages, according to representative processes as described above. This directly contrasts with conventional, continuous "chemostat" biological processes that are understood to require cell recycle in order to obtain acceptable productivity levels. Accordingly, liquid product fed to at least one stage (e.g., first stage liquid product that is fed to the second stage) may comprise the C1-fixing microorganism used in the prior (e.g., first) upstream bioreactor stage, and, for example, which has not been separated or filtered in this upstream stage. This liquid product generally further comprises culture medium, the desired end product, and other metabolites received from the prior upstream stage. Therefore, according to preferred embodiments, the liquid product of at least one bioreactor stage (e.g., the first stage liquid product) is fed to the subsequent stage, without the added expense and complexity involved in (1) the separation of the C1-fixing microorganism (e.g., using membrane separation) followed by (2) recycle of the separated microorganism to the same stage from which it is withdrawn. In preferred embodiments, processes are carried out without any separation of C1-fixing microorganism from, and/or recycle to, any of the bioreactor stages, although liquid product withdrawn from a final stage is normally separated in this manner to recover the final product(s) in a cell-free liquid. According to some embodiments, therefore, the C1-fixing microorganism and/or cell culture medium may be separated from the final stage liquid product and returned to the process (e.g., to one or more of the bioreactor stages).

Other embodiments of the invention are directed to multi-stage systems comprising a plurality of bioreactors. The bioreactors comprise a gas inlet at a first end and a gas outlet at a second end opposite the first end, such that the gas inlets and outlets allow feeding a gaseous C1-containing substrate to the plurality of bioreactors and removing gaseous products including unconverted C1 carbon source, in parallel. The bioreactors, excluding a first bioreactor and a final bioreactor (i.e., not the furthest upstream bioreactor, because it is not fed liquid product from another bioreactor, or the furthest downstream bioreactor, because liquid product withdrawn from this bioreactor is not fed to another bioreactor), comprise separate liquid inlets and outlets, for receiving a liquid product, including C1-fixing microorganism (biomass), from an adjacent, upstream bioreactor and conveying a liquid product, including C1-fixing microorganism (cells or biomass), to an adjacent, downstream bioreactor, in series.

In general, both the liquid inlets and outlets are proximate the first ends (i.e., the ends at which gaseous C1-containing substrate is received), such that liquid product can be fed to, and withdrawn from, near the bottom of the bioreactors, for example within the bottom 25%, or within the bottom 10%, of the reactor length. A liquid product outlet, for receiving a final liquid product from the final bioreactor, is likewise proximate the first end of the final bioreactor. In defining locations of various features with respect to "reactor length," this length refers to that of the section containing the reactor contents (an admixture of reactants and reaction products), commonly considered as the "reactor volume," or "reactor working volume" and this length does not include process lines (e.g., feed inlet lines or product outlet lines) that may extend above or below the reactor volume, or sections of a column or other vessel that houses a reactor but does not contain any reactor contents. For example, in the case of a cylindrical reactor, the reactor length refers to the length of axis of the cylinder. The "bottom 10%" of the reactor length refers to a range of heights, starting from the bottom of the reactor and extending upward for 10% of the reactor length. The "top 10%" of the reactor length refers to a range of heights, starting from the top of the reactor and extending downward for 10% of the reactor length. Likewise, the "bottom 1%-10%" of the reactor length refers to a range of heights, starting from a height that is 1% of the reactor length above the bottom of reactor and extends upward to a height that is 10% of the reactor length above the bottom of the reactor. The top "25%-45%" of the reactor length refers to a range of heights, starting from a height that is 25% of the reactor length below the top of reactor and extends downward to a height that is 45% of the reactor length below the top of the reactor.

Further embodiments of the invention are directed to multi-stage, biological processes for converting C1 to a desired end product. The processes comprise (i) dividing a gaseous C1-containing substrate, in parallel, among multiple bioreactor stages of the multi-stage process and (ii) successively feeding liquid products comprising a C1-fixing microorganism, in series, from a first bioreactor stage to downstream bioreactor stages. In a final stage, a final stage liquid product is withdrawn from a final bioreactor stage. In certain embodiments the final stage liquid product is withdrawn from a biomass-free liquid fraction (e.g. a liquid fraction that does not contain the C1-fixing microorganism/biomass).

In particular embodiments, the invention is directed to a multi-stage biological process for converting carbon monoxide (CO) to ethanol. The process comprises (i) dividing a CO containing substrate, in parallel among multiple stages of the multi-stage process, (ii) successively feeding liquid products comprising carboxydotrophic microorganism, in series, from a first bioreactor stage to downstream bioreactor stages. A final stage liquid product, withdrawn from a final bioreactor stage may comprise at least about 50 grams per liter (g/l) of ethanol and have an ethanol:acetic acid weight ratio of at least about 50:1. In certain embodiments the final stage liquid product is withdrawn from a biomass free liquid fraction. Particular processes may comprise at least four bioreactor stages. Such representative processes, associated with this manner of parallel gas/series liquid operation, can advantageously achieve high levels of productivity with minimal byproduct formation. In other embodiments, the invention is directed to a multi-stage biological process for converting carbon monoxide to 2,3-butanediol, with reduced ethanol productivity. In certain embodiments, the carboxydotrophic microorganism is selected from the group consisting of *Clostridium autoethanogenum, Clostridium ragsdalei* and *Clostridium ljungdahlii*.

In alternative embodiments, the invention is directed to a multi-stage biological process for converting carbon monoxide (CO) to growth dependent end products (e.g. isopropanol). The process comprises (i) dividing a CO containing substrate, in parallel among multiple stages of the multi-stage process, (ii) successively feeding liquid products comprising carboxydotrophic microorganism, in series, from a first bioreactor stage to downstream bioreactor stages. A final stage liquid product, withdrawn from a final bioreactor stage, or at least a biomass free liquid fraction thereof may comprise at least about 10 g/l of isopropanol. In certain embodiments the carboxydotrophic microorganism utilized in the isopropanol production process is a recombinant *Clostridium autoethanogenum* strain having at least one heterologous enzyme in an isopropanol biosynthesis pathway. The use of a multi-stage process of the current invention provide process for increased productivity of growth dependent end products compared to traditional two-reactor fermentation systems. In accordance with one embodiment of the invention, growth dependent end products are selected from the group consisting of isopropanol, butanol, acetone, 2-hydroxybutyric acid (2-HIBA), and isobutylene.

Overall, as discussed in greater detail below, multi-stage, biological processes as described herein can improve stability of bioconversion operations and provide greater flexibility for tailoring the performance (e.g., titers of end product and other metabolite) achieved at each stage to specific objectives. Even at lower productivities on a reactor volume basis, relative to conventional processes, the comparatively simpler construction and control systems can effectively compensate for this from an economic standpoint, through capital and/or operating cost reductions that are achieved at the commercial scale. In addition, a reduction in productivity, on a "per-reactor" basis, allows improved flexibility in terms of bioreactor dimensions, such that relatively shorter and wider vessels may be employed, having dimensions more in agreement with those of available storage tanks. For example, bioreactors of one or more stages (e.g., at least one of the first and second bioreactor stages, at least four bioreactor stages, or all bioreactor stages) may have a ratio of length to width (e.g., diameter) of less than about 15:1 (e.g., from about 2:1 to about 15:1), such as less than about 10:1 (e.g., from about 5:1 to about 10:1). An allowance for reduced productivity, in turn, permits the use of lower pressures in processes/systems as described herein. For example, bioreactors of one or more stages (e.g., at least one of the first and second bioreactor stages, at least four bioreactor stages, or all bioreactor stages) may be operated a pressure of less than about 500 kilopascal (kPa) gauge pressure (i.e., above atmospheric pressure), such as less than about 200 kPa gauge pressure, or even less than about 100 kPa gauge pressure. Multi-stage processes and systems as described herein can also advantageously achieve greater gas utilization, relative to such conventional processes, for a given mass transfer coefficient.

In multi-stage processes, the bioreactor stages described herein, or some portion thereof, may be separate sections within a single vessel. For example, such a vessel (which may be an industry standard tank having a volume of 50,000-3,000,000 liters), can include internal structures setting apart the individual bioreactor stages and directing vapor and liquid flows as described herein. For example the internal structures can be configured to flow gases and liquids in parallel and in series, respectively, through the stages. The use of bioreactor stages within a vessel may facilitate certain operating embodiments described herein, for example operation with a shared flow of gaseous products, including unconverted C1 carbon source, exiting the bioreactor stages. According to one embodiment, the bioreactor stages within a vessel may be oriented in a stacked relationship, with the first bioreactor stage being the highest in elevation and the final bioreactor stage being the lowest in elevation, thereby utilizing gravity to aid in the transfer of liquid products through the stages. The total linked bioreactor stages, which can include bioreactors, within a single vessel may range in number, and in exemplary embodiments, a vessel may include from about 4 to about 12 bioreactor stages. Internal structures can include associated piping and/or other equipment described herein with reference to FIGS. 1 and 2 (e.g., gas and liquid inlets and their connections, vapor and liquid distributors, risers, downcomers, external liquid recycle loops, inlets for liquid culture medium and other additives, etc.). Such internal structures can therefore provide overall fluid communication between the stages to achieve the desired flow configurations, including induced, internal circulation and/or external circulation using recycle loops, as described in greater detail below, thereby creating hydrodynamic conditions necessary for achieving high mass transfer and mixing at the designed gas flow rates. Such vessels may be fitted with additional liquid circulation loops, external to the entire vessel, e.g., for liquid circulation between bioreactor stages that are not necessarily adjacent (i.e., immediately upstream of, or downstream from, one another). In some embodiments, the total number of bioreactor stages required for a given biological conversion process can exceed the number of stages within a vessel, such that the process may utilize two or more vessels, one or both of which contain a plurality (e.g., two or more) of bioreactor stages.

The use of multi-stage, biological processes as described herein provides greater control over fermentation parameters and process controls. Each of the stages of the multi-stage process can be operated at varying process conditions to provide a desired end result. For example, certain stages can be operated to promote growth, and other stages can be optimized toward productivity. The use of multi-stage biological processes can result in better product titers, greater specificity to desired end products, improved gas uptake, and greater flexibility toward C1-containing substrates of various compositions.

These and other embodiments, aspects, and advantages relating to the present invention are apparent from the following Detailed Description.

BRIEF DESCRIPTION OF THE DRAWINGS

A more complete understanding of the exemplary embodiments of the present invention and the advantages thereof may be acquired by referring to the following description in consideration of the accompanying figures, in which similar features are identified by similar reference numbers (e.g., bioreactor 100a of FIG. 1 and bioreactor 100 of FIG. 2).

FIGS. 1-5 should be understood to present an illustration of the disclosure and/or principles involved. In order to facilitate explanation and understanding, simplified process flow schemes and equipment are depicted in FIGS. 1 and 2, and these figures are not necessarily drawn to scale. Details including valves, instrumentation, and other equipment and systems not essential to the understanding of the disclosure are not shown. As is readily apparent to one of skill in the art having knowledge of the present disclosure, methods for the biological conversion of C1-containing substrates according to other embodiments of the invention, will have configurations and components determined, in part, by their specific use.

DETAILED DESCRIPTION

Figure 1:
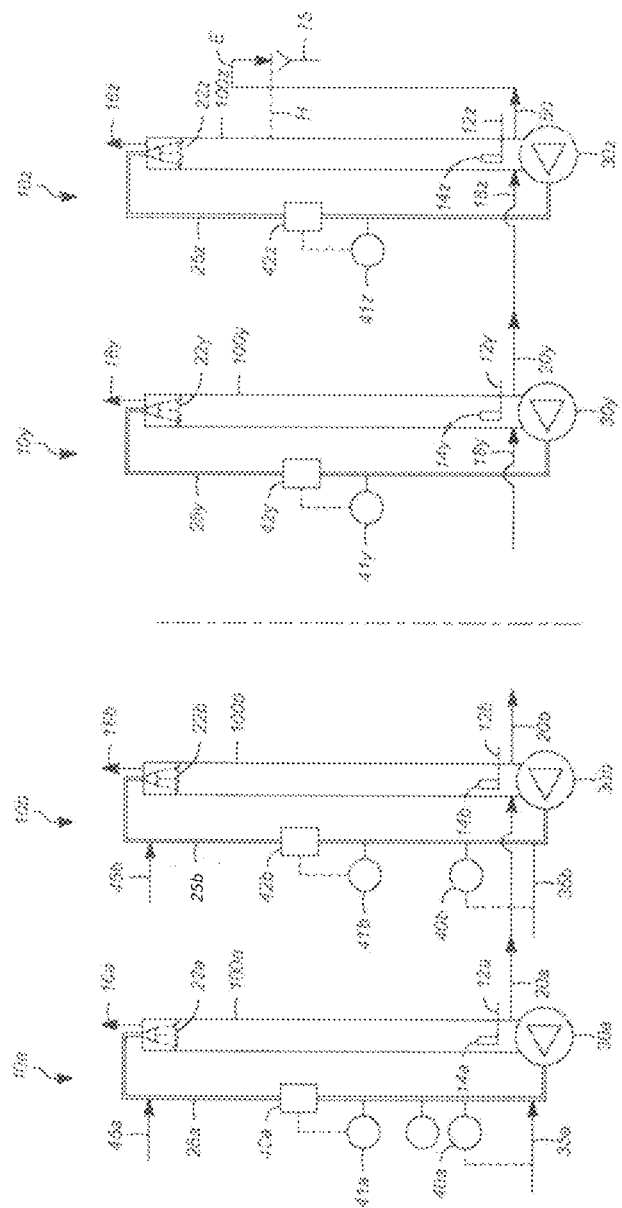
FIG. 1 depicts a representative process utilizing at least two upstream bioreactors and two downstream bioreactors, with similar intervening bioreactors being omitted for simplicity.

The present invention relates to processes for producing a desired end product, by feeding C1 carbon source in a gaseous C1-containing substrate in parallel to multiple bioreactor stages that are used, in turn, to process liquid products of these stages in series. In operation, each of the bioreactors comprises a liquid culture medium containing a C1-fixing microorganism. In addition to the desired end product, processes as described herein additionally generate undesired or less desired metabolites. Representative C1-fixing microorganisms, are those from the genus *Moorella, Clostridia, Ruminococcus, Acetobacterium, Eubacterium, Butyribacterium, Oxobacter, Methanosarcina, Methanosarcina,* and *Desulfotomaculum*. Particular examples of microorganisms that are *Clostridia* include *C. jundahlii, C. autoethanogenum, C. ragsdalei*, and *C. beijerenckei*.

Representative C1-containing substrates include broadly any C1 carbon source-containing gas, in which at least one C1 carbon source selected from the group consisting of CO, $CO_2$ and $CH_4$, can be made available to one or more strains of C1-fixing microorganisms for growth and/or fermentation. Such C1-containing substrates preferably do not include contaminants to the extent that such contaminants might have an adverse effect on the growth of the C1-fixing microorganism (e.g., one or more contaminant(s) are not present in concentrations or amounts such that the growth rate is reduced by more than 10% under a given set of conditions, compared to the growth rate under the same conditions, but without the contaminant(s)).

Representative C1 containing substrates as described herein, include broadly any C1-carbon source. A C1-carbon source refers a one carbon-molecule that serves as a partial or sole carbon source for the microorganisms of the invention. For example, a C1-carbon source may comprise one or more of CO, $CO_2$, $CH_4$. Preferably, the C1-carbon source comprises one or both of CO and $CO_2$. The substrate may further comprise other non-carbon components, such as $H_2$, $N_2$, or electrons.

The C1 containing substrate may contain a significant proportion of CO, preferably at least about 5% to about 99.5% CO by volume. Such substrates are often produced as waste products of industrial processes such as steel manufacturing processes or non-ferrous product manufacturing process. Other processes in which gaseous CO-containing substrates are generated include petroleum refining processes, biofuel production processes (e.g., pyrolysis processes and fatty acid/triglyceride hydroconversion processes), coal and biomass gasification processes, electric power production processes, carbon black production processes, ammonia production processes, methanol production processes, and coke manufacturing processes. A number of chemical industry effluents, as well as syngases (containing both CO and $H_2$) produced from a variety of substrates, can likewise serve as potential CO-containing substrates. Specific examples include effluents from the production of phosphate and chromate. Advantageously, wastes (e.g., waste gases) from these processes may be used as described herein for the beneficial production of useful end products such as ethanol The substrate and/or C1-carbon source may be or may be derived from a waste or off gas obtained as a byproduct of an industrial process or from some other source, such as from automobile exhaust fumes or biomass gasification. In certain embodiments, the industrial process is selected from the group consisting of ferrous metal products manufacturing, such as a steel mill manufacturing, non-ferrous products manufacturing, petroleum refining processes, coal gasification, electric power production, carbon black production, ammonia production, methanol production, and coke manufacturing. In these embodiments, the substrate and/or C1-carbon source may be captured from the industrial process before it is emitted into the atmosphere, using any convenient method.

The substrate and/or C1-carbon source may be or may be derived from syngas, such as syngas obtained by gasification of coal or refinery residues, gasification of biomass or lignocellulosic material, or reforming of natural gas. In another embodiment, the syngas may be obtained from the gasification of municipal solid waste or industrial solid waste.

In connection with substrates and/or C1-carbon sources, the term "derived from" refers to a substrate and/or C1-carbon source that is somehow modified or blended. For example, the substrate and/or C1-carbon source may be treated to add or remove certain components or may be blended with streams of other substrates and/or C1-carbon sources.

The composition of the substrate may have a significant impact on the efficiency and/or cost of the reaction. For example, the presence of oxygen ($O_2$) may reduce the efficiency of an anaerobic fermentation process. Depending on the composition of the substrate, it may be desirable to treat, scrub, or filter the substrate to remove any undesired impurities, such as toxins, undesired components, or dust particles, and/or increase the concentration of desirable components.

The substrate generally comprises at least some amount of CO, such as about 1, 2, 5, 10, 20, 30, 40, 50, 60, 70, 80, 90, or 100 mol % CO. The substrate may comprise a range of CO, such as about 20-80, 30-70, or 40-60 mol % CO. Preferably, the substrate comprises about 40-70 mol % CO (e.g., steel mill or blast furnace gas), about 20-30 mol % CO (e.g., basic oxygen furnace gas), or about 15-45 mol % CO (e.g., syngas). In some embodiments, the substrate may comprise a relatively low amount of CO, such as about 1-10 or 1-20 mol % CO. The microorganism of the invention typically converts at least a portion of the CO in the substrate to a product. In some embodiments, the substrate comprises no or substantially no CO.

The substrate may comprise some amount of $H_2$. For example, the substrate may comprise about 1, 2, 5, 10, 15, 20, or 30 mol % $H_2$. In some embodiments, the substrate may comprise a relatively high amount of $H_2$, such as about 60, 70, 80, or 90 mol % $H_2$. In further embodiments, the substrate comprises no or substantially no $H_2$.

The substrate may comprise some amount of $CO_2$. For example, the substrate may comprise about 1-80 or 1-30 mol % $CO_2$. In some embodiments, the substrate may comprise less than about 20, 15, 10, or 5 mol % $CO_2$. In another embodiment, the substrate comprises no or substantially no $CO_2$.

Although the substrate is typically gaseous, the substrate may also be provided in alternative forms. For example, the substrate may be dissolved in a liquid saturated with a CO-containing gas using a microbubble dispersion generator. By way of further example, the substrate may be adsorbed onto a solid support.

A "microorganism" is a microscopic organism, especially a bacterium, archea, virus, or fungus. The microorganism of the invention is typically a bacterium. As used herein, recitation of "microorganism" should be taken to encompass "bacterium."

The microorganism of the invention may be further classified based on functional characteristics. For example, the microorganism of the invention may be or may be derived from a C1-fixing microorganism, an anaerobe, an acetogen, an ethanologen, a carboxydotroph, and/or a methanotroph. Table 1 provides a representative list of microorganisms and identifies their functional characteristics.

TABLE 1

|  | C1-fixing | Anaerobe | Acetogen | Ethanologen | Autotroph | Carboxydotroph | Methanotroph |
|---|---|---|---|---|---|---|---|
| *Acetobacterium woodii* | + | + | + | +/− [1] | − | +/− [2] | − |
| *Alkalibaculum bacchii* | + | + | + | + | + | + | − |
| *Blautia producta* | + | + | + | − | + | + | − |
| *Butyribacterium methylotrophicum* | + | + | + | + | + | + | − |
| *Clostridium aceticum* | + | + | + | − | + | + | − |
| *Clostridium autoethanogenum* | + | + | + | + | + | + | − |
| *Clostridium carboxidivorans* | + | + | + | + | + | + | − |
| *Clostridium coskatii* | + | + | + | + | + | + | − |
| *Clostridium drakei* | + | + | + | − | + | + | − |
| *Clostridium formicoaceticum* | + | + | + | − | + | + | − |
| *Clostridium ljungdahlii* | + | + | + | + | + | + | − |
| *Clostridium magnum* | + | + | + | − | + | +/− [3] | − |
| *Clostridium ragsdalei* | + | + | + | + | + | + | − |
| *Clostridium scatologenes* | + | + | + | − | + | + | − |
| *Eubacterium limosum* | + | + | + | − | + | + | − |
| *Moorella thermautotrophica* | + | + | + | + | + | + | − |
| *Moorella thermoacetica* (formerly *Clostridium thermoaceticum*) | + | + | + | − [4] | + | + | − |
| *Oxobacter pfennigii* | + | + | + | − | + | + | − |
| *Sporomusa ovata* | + | + | + | − | + | +/− [5] | − |
| *Sporomusa silvacetica* | + | + | + | − | + | +/− [6] | − |

TABLE 1-continued

| | C1-fixing | Anaerobe | Acetogen | Ethanologen | Autotroph | Carboxydotroph | Methanotroph |
|---|---|---|---|---|---|---|---|
| *Sporomusa sphaeroides* | + | + | + | − | + | +/− [7] | − |
| *Thermoanaerobacter kiuvi* | + | + | + | − | + | − | − |

[1] *Acetobacterium woodi* can produce ethanol from fructose, but not from gas.
[2] It has been reported that *Acetobacterium woodi* can grow on CO, but the methodology is questionable.
[3] It has not been investigated whether *Clostridium magnum* can grow on CO.
[4] One strain of *Moorella thermoacetica*, *Moorella* sp. HUC22-1, has been reported to produce ethanol from gas.
[5] It has not been investigated whether *Sporomusa ovata* can grow on CO.
[6] It has not been investigated whether *Sporomusa silvacetica* can grow on CO.
[7] It has not been investigated whether *Sporomusa sphaeroides* can grow on CO.

"C1" refers to a one-carbon molecule, for example, CO, $CO_2$, $CH_4$, or $CH_3OH$. "C1-oxygenate" refers to a one-carbon molecule that also comprises at least one oxygen atom, for example, CO, $CO_2$, or $CH_3OH$. "C1-carbon source" refers a one carbon-molecule that serves as a partial or sole carbon source for the microorganism of the invention. For example, a C1-carbon source may comprise one or more of CO, $CO_2$, $CH_4$. Preferably, the C1-carbon source comprises one or both of CO and $CO_2$. A "C1-fixing microorganism" is a microorganism that has the ability to produce one or more products from a C1-carbon source. Typically, the microorganism of the invention is a C1-fixing bacterium. In a preferred embodiment, the microorganism of the invention is derived from a C1-fixing microorganism identified in Table 1.

An "anaerobe" is a microorganism that does not require oxygen for growth. An anaerobe may react negatively or even die if oxygen is present above a certain threshold. Typically, the microorganism of the invention is an anaerobe. In a preferred embodiment, the microorganism of the invention is derived from an anaerobe identified in Table 1.

An "acetogen" is a microorganism that produces or is capable of producing acetate (or acetic acid) as a product of anaerobic respiration. Typically, acetogens are obligately anaerobic bacteria that use the Wood-Ljungdahl pathway as their main mechanism for energy conservation and for synthesis of acetyl-CoA and acetyl-CoA-derived products, such as acetate (Ragsdale, Biochim Biophys Acta, 1784: 1873-1898, 2008). Acetogens use the acetyl-CoA pathway as a (1) mechanism for the reductive synthesis of acetyl-CoA from $CO_2$, (2) terminal electron-accepting, energy conserving process, (3) mechanism for the fixation (assimilation) of $CO_2$ in the synthesis of cell carbon (Drake, Acetogenic Prokaryotes. In: The Prokaryotes, 3rd edition, p. 354, New York, N.Y. 2006). All naturally occurring acetogens are C1-fixing, anaerobic, autotrophic, and non-methanotrophic. Typically, the microorganism of the invention is an acetogen. In a preferred embodiment, the microorganism of the invention is derived from an acetogen identified in Table 1.

An "ethanologen" is a microorganism that produces or is capable of producing ethanol. Typically, the microorganism of the invention is an ethanologen. In a preferred embodiment, the microorganism of the invention is derived from an ethanologen identified in Table 1.

An "autotroph" is a microorganism capable of growing in the absence of organic carbon. Instead, autotrophs use inorganic carbon sources, such as CO and/or $CO_2$. Typically, the microorganism of the invention is an autotroph. In a preferred embodiment, the microorganism of the invention is derived from an autotroph identified in Table 1.

A "carboxydotroph" is a microorganism capable of utilizing CO as a sole source of carbon. Typically, the microorganism of the invention is a carboxydotroph. In a preferred embodiment, the microorganism of the invention is derived from a carboxydotroph identified in Table 1.

A "methanotroph" is a microorganism capable of utilizing methane as a sole source of carbon and energy. In certain embodiments, the microorganism of the invention is derived from a methanotroph.

More broadly, the microorganism of the invention may be derived from any genus or species identified in Table 1.

In a preferred embodiment, the microorganism of the invention is derived from the cluster of *Clostridia* comprising the species *Clostridium autoethanogenum*, *Clostridium ljungdahlii*, and *Clostridium ragsdalei*. These species were first reported and characterized by Abrini, Arch Microbiol, 161: 345-351, 1994 (*Clostridium autoethanogenum*), Tanner, Int J System Bacteriol, 43: 232-236, 1993 (*Clostridium ljungdahlii*), and Huhnke, WO 2008/028055 (*Clostridium ragsdalei*).

These three species have many similarities. In particular, these species are all C1-fixing, anaerobic, acetogenic, ethanologenic, and carboxydotrophic members of the genus *Clostridium*. These species have similar genotypes and phenotypes and modes of energy conservation and fermentative metabolism. Moreover, these species are clustered in clostridial rRNA homology group I with 16S rRNA DNA that is more than 99% identical, have a DNA G+C content of about 22-30 mol %, are gram-positive, have similar morphology and size (logarithmic growing cells between 0.5-0.7×3-5 µm), are mesophilic (grow optimally at 30-37° C.), have similar pH ranges of about 4-7.5 (with an optimal pH of about 5.5-6), lack cytochromes, and conserve energy via an Rnf complex. Also, reduction of carboxylic acids into their corresponding alcohols has been shown in these species (Perez. Biotechnol Bioeng, 110:1066-1077, 2012). Importantly, these species also all show strong autotrophic growth on CO-containing gases, produce ethanol and acetate (or acetic acid) as main fermentation products, and produce small amounts of 2,3-butanediol and lactic acid under certain conditions.

However, these three species also have a number of differences. These species were isolated from different sources: *Clostridium autoethanogenum* from rabbit gut, *Clostridium ljungdahlii* from chicken yard waste, and *Clostridium ragsdalei* from freshwater sediment. These species differ in utilization of various sugars (e.g., rhamnose, arabinose), acids (e.g., gluconate, citrate), amino acids (e.g., arginine, histidine), and other substrates (e.g., betaine, butanol). Moreover, these species differ in auxotrophy to certain vitamins (e.g., thiamine, biotin). These species have differences in nucleic and amino acid sequences of Wood-Ljungdahl pathway genes and proteins, although the general organization and number of these genes and proteins has been found to be the same in all species (Köpke, Curr Opin Biotechnol, 22: 320-325, 2011).

Thus, in summary, many of the characteristics of *Clostridium autoethanogenum*, *Clostridium ljungdahlii*, or *Clostridium ragsdalei* are not specific to that species, but are rather general characteristics for this cluster of C1-fixing, anaerobic, acetogenic, ethanologenic, and carboxydotrophic members of the genus *Clostridium*. However, since these species are, in fact, distinct, the genetic modification or manipulation of one of these species may not have an identical effect in another of these species. For instance, differences in growth, performance, or product production may be observed.

The microorganism of the invention may also be derived from an isolate or mutant of *Clostridium autoethanogenum*, *Clostridium ljungdahlii*, or *Clostridium ragsdalei*. Isolates and mutants of *Clostridium autoethanogenum* include JA1-1 (DSM10061) (Abrini, Arch Microbiol, 161: 345-351, 1994), LBS1560 (DSM19630) (WO 2009/064200), and LZ1561 (DSM23693). Isolates and mutants of *Clostridium ljungdahlii* include ATCC 49587 (Tanner, Int J Syst Bacteriol, 43: 232-236, 1993), PETCT (DSM13528, ATCC 55383), ERI-2 (ATCC 55380) (U.S. Pat. No. 5,593,886), C-01 (ATCC 55988) (U.S. Pat. No. 6,368,819), 0-52 (ATCC 55989) (U.S. Pat. No. 6,368,819), and OTA-1 (Tirado-Acevedo, Production of bioethanol from synthesis gas using *Clostridium ljungdahlii*. PhD thesis, North Carolina State University, 2010). Isolates and mutants of *Clostridium ragsdalei* include PI 1 (ATCC BAA-622, ATCC PTA-7826) (WO 2008/028055).

The microorganism of the invention may be cultured to produce one or more products. For instance, *Clostridium autoethanogenum* produces or can be engineered to produce ethanol (WO 2007/117157), acetate (WO 2007/117157), butanol (WO 2008/115080 and WO 2012/053905), butyrate (WO 2008/115080), 2,3-butanediol (WO 2009/151342), lactate (WO2011/112103), butene (WO2012/024522), butadiene (WO2012/024522), methyl ethyl ketone (2-butanone) (WO 2012/024522 and WO 2013/185123), ethylene (WO 2012/026833), acetone (WO 2012/115527), isopropanol (WO 2012/115527), lipids (WO 2013/036147), 3-hydroxypropionate (3-HP) (WO 2013/180581), isoprene (WO 2013/180584), fatty acids (WO 2013/191567), 2-butanol (WO 2013/185123), 1,2-propanediol (WO 2014/0369152), and 1-propanol (WO 2014/0369152). In addition to one or more target products, the microorganism of the invention may also produce ethanol, acetate, and/or 2,3-butanediol. In certain embodiments, microbial biomass itself may be considered a product In the context of an acidic metabolite that is acetic acid, the terms "acetic acid" or "acetate" refer to the total acetate present in the culture medium, either in its anionic (dissociated) form (i.e., as acetate ion or $CH_3COO^-$) or in the form of free, molecular acetic acid ($CH_3COOH$), with the ratio these forms being dependent upon the pH of the system. As described below, a basic neutralizing agent such as aqueous sodium hydroxide (NaOH) may be used to control the pH of the culture medium in a given bioreactor (e.g., to a pH set point value that may be any specific pH valve between pH=4.5 and pH=8.0), by neutralizing acetic acid. Representative pH ranges at which bioreactors are maintained for carrying out the processes described herein are from about 4.0 to about 8.0, such as from about 5.0 to about 6.5.

"Liquid product" as used herein refers to a liquid stream which is fed to at least one stage of the multi-stage process (e.g. a first stage liquid product that is fed to a second stage). The liquid product contains (i) culture medium containing C1-fixing microorganism, (ii) desired end product, and (iii) other metabolites. The liquid product can further contain dissolved C1-containing substrate. The "final stage liquid product" as used herein is a liquid product withdrawn from the final reactor stage of a multi-stage process. The final stage liquid product is typically withdrawn from a biomass free portion liquid fraction of the final stage.

"End products" or "desired end products" as used herein refer to metabolites produced by the microorganisms of the invention. The microorganisms of the invention may be cultured to produce one or more products selected from the group consisting of to produce ethanol, acetate, butanol, butyrate, 2,3-butanediol, lactate, butane, butadiene, methyl ethyl ketone (2-butanone), ethylene, acetone, isopropanol, lipids, 3-hydroxypropionate (3-HP), isoprene, fatty acids, 2-butanol, 1,2-propanediol, and 1-propanol "Growth dependent products" as used herein refer to metabolites which exhibit a production rate that is directly proportional with the production rate of biomass. Examples of growth dependent products include, but are not limited to, isopropanol, acetate, acetone, 2-hydroxybutyric acid (2-HIBA) and isobutylene.

One of the benefits of the multi-stage reactor process is the ability to tailor the fermentation process toward at least one desired end product. It would be understood, that depending on the process parameters provided, a desired end product in one fermentation process, may be an undesired metabolite in a different fermentation process operated under different process condition. For example, in a multi-stage process directed to ethanol production, ethanol is a desired end product, however in a multi-stage process directed to isopropanol production, isopropanol is the desired end product, and ethanol is a by-product metabolite.

As described below, a specific type of bioreactor that is particularly useful in the practice of the present invention is a circulated loop reactor that relies on a density gradient between a relatively low density section within a riser and a relatively high density section within one or more, internal or external downcomers. Both the riser and downcomer sections include liquid culture medium in a continuous liquid phase zone, but the gaseous CO-containing substrate is normally distributed (e.g., sparged) into the bottom of the riser section. Rising gas bubbles are confined to this section during their upward movement through the continuous liquid phase zone, until any unconsumed and undissolved gas is released into a continuous gas phase zone (i.e., vapor space or headspace) above the liquid level. The downward liquid circulation, through either an internal or external liquid downcomer, may be induced or aided by a loop pump. In some cases, however, a loop pump is not used for at least one of the plurality bioreactors, and often a loop pump is not used for most or even all of the bioreactors, thereby relying on the density-induced circulation alone and advantageously conserving energy costs.

The term "bioreactor," as well as any bioreactor that may be included as part of a "bioreactor stage," is not limited to a circulated loop reactor, but more broadly includes any suitable vessel, or section within a vessel, for maintaining a liquid volume of culture medium with carboxydotrophic microorganism that may be used to carry out the biological processes described herein, which may also be referred to as fermentation processes to the extent that they are generally conducted anaerobically. Particular types of bioreactors can include any vessels suitable for two-phase (gas-liquid) contacting, for example counter-current flow reactors (e.g., with an upwardly-flowing vapor phase and downwardly-flowing liquid phase) or co-current flow reactors (e.g., with upwardly-flowing gas and liquid phases). In such two-phase contacting vessels, it is possible for the liquid phase to be the continuous phase, as in the case of gas bubbles flowing through a moving column of liquid. Otherwise, it is possible for the vapor phase to be the continuous phase, as in the case of a dispersed liquid (e.g., in the form of droplets) flowing through a vapor space. In some embodiments, described more fully below, different zones of a bioreactor may be used to contain a continuous liquid phase and a continuous gas phase.

Specific examples of bioreactors include Continuous Stirred Tank Reactors (CSTRs), Immobilized Cell Reactors (ICRs), Trickle Bed Reactors (TBRs), Moving Bed Biofilm Reactor (MBBRs), Bubble Columns, Gas Lift Fermenters, and Membrane Reactors such as Hollow Fiber Membrane Bioreactors (HFMBRs). Suitable bioreactors may include static mixers, or other vessels and/or devices (e.g., towers or piping arrangements), suitable for contacting the gaseous C1-containing substrate with the liquid bacterial culture medium (e.g., with dissolution and mass transport kinetics favorable for carrying out the biological conversion). The phrases "plurality of bioreactors" or bioreactors that may be included in a "plurality of bioreactor stages" are meant to include bioreactors of more than a single type, although in some cases the plurality of bioreactors may be of one type (e.g., circulated loop reactors).

Some suitable process streams, operating parameters, and equipment for use in the biological processes described herein are described in U.S. patent application Publication No. US2011/0212433, which is hereby incorporated by reference in its entirety.

The present invention is more particularly associated with the discovery of biological processes for converting C1 carbon sources to valuable end products, involving the parallel-gas, series-liquid processing configurations as described herein, utilizing a plurality of bioreactor stages. Advantageously, one or more membrane systems for cell (microorganism or biomass) separation and recycle to a given bioreactor stage can be avoided, while achieving high overall productivity (e.g., over two or more bioreactors) of the desired end product with very low overall byproduct formation.

In particular examples, the invention is associated with processes for converting CO to ethanol, using a multi-stage process as described herein. In certain embodiments, the C1-fixing microorganism is a carboxydotrophic microorganism. More specifically the carboxydotrophic microorganism is selected from the group consisting of Clostridium autoethanogenum, Clostridium ragsdalei, and Clostridium ljungdahlii. In particular embodiments, the carboxydotrophic microorganism is Clostridium autoethanogenum strain DSM23693. Representative ethanol concentrations in an intermediate stage liquid product or final stage liquid product, withdrawn from a bioreactor stage positioned downstream of other stages (e.g., the final bioreactor stage) are generally at least about 40 grams per liter (grams/liter or g/l) (e.g., from about 40 to about 95 g/l), typically at least about 50 g/l (e.g., from about 50 to about 80 g/l), and often at least about 60 g/l (e.g., from about 60 to about 75 g/l). Representative weight ratios of ethanol:acetic acid in such an intermediate stage liquid product or final stage liquid product are generally at least about 50:1 (e.g., from about 50:1 to about 1000:1), typically at least about 75:1 (e.g., from about 75:1 to about 500:1), and often at least about 100:1 (e.g., from about 100:1 to about 250:1). These characteristics of the liquid product can refer, more particularly, to liquid product withdrawn from an intermediate stage bioreactor or the final stage bioreactor, and following a separation (e.g., membrane filtration) to remove the carboxydotrophic microorganism (cells or biomass). In general, the analytical methods (e.g., gas chromatograph (GC) or high pressure liquid chromatography, HPLC) used to determine metabolite concentrations require cell-free samples.

In addition to achieving high overall ethanol productivity with minimal overall by-product formation, multi-stage processes as described herein can further provide favorable overall CO utilization. The overall CO utilization refers to the percentage of CO that is input to the multi-stage process (e.g., the total CO input to the bioreactors) and utilized in the conversion to desired product(s) (e.g., ethanol) and other metabolites of the microorganism. If the combined composition of all gas streams exiting the process (i.e., the gaseous products) is known or can be calculated (e.g., based on the flow rates and compositions of individual gas stream(s) exiting each of the bioreactors used), then the overall CO utilization may be calculated as:

$$1-(\text{rate of CO exiting the multi-stage process})/(\text{rate of CO input to the multi-stage process})$$

The overall CO utilization is determined on a "per pass" or "once-through" basis, without accounting for the use of gaseous product recycle (and added expense) that can provide higher total utilization values. According to representative embodiments, the CO utilization by the carboxydotrophic microorganism is generally at least about 35% (e.g., from about 35% to about 85%), typically at least about 50% (e.g., from about 50% to about 80%), and often at least about 60% (e.g., from about 60% to about 75%). In some cases, CO utilization may be at least about 70%.

In accordance with one embodiment of the invention, the fermentation parameters of the multi stage process are adjusted to increase production of at least one growth dependent product. In one embodiment, the fermentation parameters of the multi-stage process are adjusted to increase specificity of the process to isopropanol. In particular examples, the invention is associated with processes for converting CO to isopropanol, using a multi-stage process as described herein. In certain embodiments, the C1-fixing microorganism a recombinant Closiridium autoethanogenum strain. In certain embodiments the recombinant microorganism is adapted to express or over express at least one enzyme in the isopropanol biosynthesis pathway.

Figure 5A:
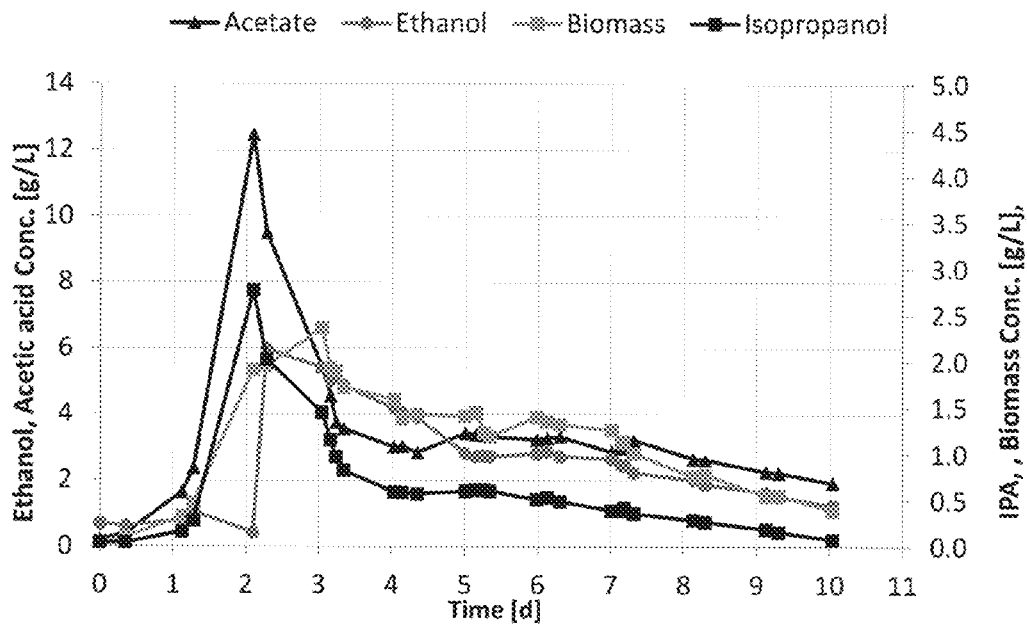
FIG. 5A is a graph showing the metabolite profile of an isopropanol fermentation
Figure 5B:
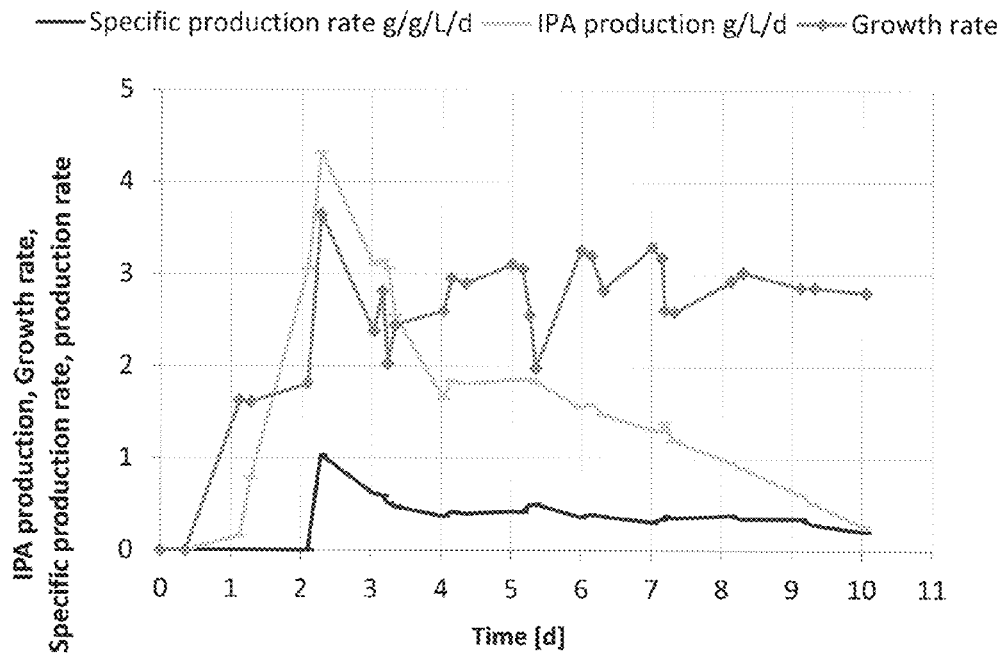
FIG. 5B is a graph showing isopropanol productivity rates.

Embodiments of the present invention relate to methods for increasing productivity of metabolites which exhibit a production rate that is directly proportional with the production rate of biomass (e.g. growth dependent products). As demonstrated in FIGS. 5A and 5B the production rate of acetone and/or Isopropanol is linked the growth phase of the fermentation. As demonstrated in the graphs. FIG. 5A shows a strong correlation between Acetate and Isopropanol concentrations in a fermentation process, in a CSTR. Both Acetate and Isopropanol concentrations increase during the initial growth phase of the fermentation (days 1 and 2). As the growth phase begins to level out, both acetate and isopropanol concentrations drop. FIG. 5B shows the relationship between the productivity of isopropanol and the growth rate. It is clearly demonstrated that isopropanol reaches its highest productivity at the highest growth rate.

It has been shown that the enzyme CtfAB catalyzes the formation of acetoacetate by transfer of the CoA moiety from acetoacetyl-CoA to acetate leading to the formation of acetoacetate and acetyl-CoA. This enzymes activity is dependent on the availability of acetate. The Km values of CtfAB's for acetate have been reported to be anywhere from 24 mM (1.4 g/L) to 1200 mM. (71 g/L). The KM value is the substrate concentration at which the enzyme functions at half it's maximum rate. Therefor in order for the CtfAB to be active to half it's maximum rate, between 1.4-71 g/L of acetate is required. The inventors approximate that at least 14 g/L of acetate is required in the cell, to ensure that acetate is not the limiting substrate in an isopropanol fermentation process.

Multi-stage bioreactor process, as provided by the present invention provide greater adaptability of the process. By making process parameter adjustments to various stages of the multi-stage process, the desired outcome can be varied. For example, the multi-stage process can be tailored to have greater product specificity toward desired end products (for example ethanol, or 2,3-butanediol, or growth dependent products such as isopropanol). Examples of process parameters that can be controlled or adjusted throughout the multi-stage bioreactor process include C1-containing substrate composition, C1-containing substrate flow rates, temperature, pressure, bacterial dilution rates, and liquid culture media composition.

Examples of suitable manipulations include, providing C1-containing substrate to different stages of the multi-stage process at varying flow rates, providing C1-containing substrates having varying composition to different stages of the multi-stage process, providing liquid culture media having varying composition to different stages of the multi-stage process (e.g. providing a liquid culture media that has a limited composition to at least stages of the multi-stage process), altering the temperature between different stages of a multi-stage system (e.g. decreasing the temperature from the first reactor stage and subsequent reactor stages), altering the bacterial dilution rate between stages of the multi-stage reactor process), altering the mixing rate within each stage of the multi-stage process (e.g. by altering pump speed of liquid distribution devices, or by modifying either the internal reactor design or dimensions).

Importantly, as described above, the above performance parameters may be achieved in multi-stage bioreactor processes in which it is not necessary to separate and recycle carboxydotrophic microorganism that is withdrawn in the liquid product of one (upstream) bioreactor and fed to another (downstream) bioreactor, as is practiced in conventional, continuous biological conversion processes. In general, therefore, liquid product withdrawn from an upstream bioreactor stage and fed to a given bioreactor stage may comprise carboxydotrophic microorganism used in the upstream (prior) bioreactor stage, as this microorganism is not separated from one or more, and preferably all, of the liquid products being transferred from one stage to the next in series. Liquid products that are fed to a given bioreactor stage generally further comprise culture medium, the desired end product, and other metabolites received from the upstream (prior) stage.

Therefore, according to embodiments described herein that advantageously avoid the use of conventional cell separation and recycle (e.g., membrane) systems, the liquid product withdrawn from an upstream bioreactor stage is not subjected to separation of carboxydotrophic microorganism and recycle of the separated carboxydotrophic microorganism to the upstream bioreactor stage from which it was withdrawn. This characterizing feature of processes and system described herein, however, does not preclude the use various intermediate steps, following the withdrawal of liquid product from an upstream stage and prior to feeding it to a given bioreactor stage, which steps may or may not affect the composition of the liquid product. Such intermediate steps include for example (i) separating a portion of the liquid product (e.g., for sampling purposes), optionally in combination with filtration of the separated portion (e.g., as necessary to perform an analytical method), (ii) mixing the liquid product (e.g., with culture medium, particular nutrients, or process additives such as surfactants), and/or (iii) reacting the liquid product (e.g., with neutralizing agent, such as $NH_4OH$ or NaOH, to increase pH). In some embodiments, however, liquid product withdrawn from a given bioreactor stage may be fed to a given biorcactor stage without undergoing (i), (ii), and/or (iii), described above, or without undergoing some combination of these.

FIG. 1 depicts a representative, multi-stage bioconversion process according to a particular embodiment of the present disclosure, comprising at least four interconnected bioreactor stages ($10a$, $10b$, . . . $10y$, $10z$), with the dashed line between the second and third stages ($10a$, $10y$) being used to indicate that one or more, additional intermediate stages may be incorporated into a given, multi-stage system in a similar manner and with similar equipment and connections. As described more fully below, gaseous C1-containing substrate can be fed in parallel to the stages, whereas liquid products, which can include biomass, can be fed successively from a first bioreactor stage ($10a$) to a final bioreactor stage ($10z$), from which a final stage liquid product may be withdrawn, having the representative characteristics in this liquid product, or at least in a biomass free fraction thereof, as described above.

According to representative processes, gaseous C1-containing substrate is fed to the bioreactor stages through gas inlets ($12a$, $12b$, $12y$, $12z$) positioned proximate the bottom ends of vertically extending bioreactors ($100a$, $100b$, $100y$, $100z$) of each bioreactor stage. For example, the gas inlets may extend into their respective bioreactors within the bottom 25%, and preferably within the bottom 10%, of the length of their respective bioreactors. The gas inlets will normally extend into their respective bioreactors, to gas distribution devices that may be disposed centrally within the bioreactors at a height corresponding generally to within these percentages of reactor length. Particular gas distribution devices include spargers ($14a$, $14b$, $14y$, $14z$), with which the gas inlets may be in fluid communication, within one or more of the bioreactors, proximate their respective first ends. Gaseous products, including unconverted C1 carbon source and any gaseous impurities of the C1-containing substrate (e.g., $H_2$), that are not utilized in the bioconversion reaction, are withdrawn from each bioreactor and exit through gas outlets ($16a$, $16b$, $16y$, $16z$) positioned proximate the top ends of the bioreactors, opposite the bottom ends. The gas outlets may extend into their respective bioreactors within the top 25%, and preferably within the top 10%, of the length of their respective bioreactors, or otherwise gaseous products may be withdrawn from the tops of their respective bioreactors, without the gas outlets extending into their respective bioreactors at all.

Intermediate bioreactors ($100b$, $100y$) each include liquid inlets ($18b$, $18y$) and liquid outlets ($20b$, $20y$) that can receive liquid product withdrawn from the immediately adjacent upstream bioreactor and convey liquid product to the immediately adjacent downstream bioreactor. For example, bioreactor $100b$ of the second stage has liquid inlet $18b$ for receiving liquid product withdrawn from bioreactor $100a$ of the first stage (e.g., through its liquid outlet $20a$) and liquid outlet $20b$ for conveying liquid product to a bioreactor (not shown) of a third stage (e.g., through its liquid inlet, not shown). Bioreactor $100a$ (i.e., the bioreactor of the first stage $10a$) does not have an upstream bioreactor, and therefore lacks a liquid inlet that is specifically for receiving liquid product from an adjacent, upstream bioreactor. Bioreactor 100z (i.e., the bioreactor of the final stage 10z) does not have a downstream bioreactor, and therefore lacks a liquid outlet specifically for conveying liquid product to an adjacent, downstream bioreactor. However, final bioreactor 100z includes liquid product outlet 50 for withdrawing a final stage liquid product, for example having the representative characteristics in terms of its composition, as described above. The transfer of liquid product (or "broth") to/from successive stages via inlets and outlets (20a . . . 20y and 18a . . . 18z) may occur through small bore open pipes (e.g., having inner diameters from about 1 mm to about 12 mm) in fluid communication with these inlets and outlets.

As with the case of liquid outlets (20b, 20y) of bioreactors of intermediate stages, liquid product outlet 50 of bioreactor 100z of the final stage is positioned proximate the bottom end of the bioreactor. Following its withdrawal from bioreactor 100z, the final stage liquid product that is withdrawn in liquid product outlet 50 may be passed to, and optionally extend above, height H, corresponding to the working, ungassed liquid level (i.e., liquid level that would exist without gas hold-up). That is, the highest elevation E to which the final stage liquid product extends may be at or above height H. Height H may be adjustable, and may correspond substantially to height H of siphon breaker 75 or other type of liquid take-off point. In the embodiment of FIG. 1, therefore, liquid product outlet 50 is in fluid communication with siphon breaker 75 that is adjustable in height, relative to bioreactors (100a, 100b . . . 100y, 100z) of the multi-stage process. Elevation E and height H may be regulated to govern the liquid level or hydraulic head of bioreactor 100z of the final stage, and preferably other bioreactors, to the extent that they may be hydraulically linked, without disruption of a liquid-full (or continuous liquid phase) condition in liquid inlets and outlets (20a . . . 20y and 18a . . . 18z) transferring liquid product in series from one stage to the next. Elevation E and/or height H may therefore govern the liquid level in one or more, and preferably all, bioreactors (100a . . . 100z), and in particular may govern the levels of gas/liquid interfaces (22a . . . 22z) in their respective bioreactors.

In the specific embodiment depicted in FIG. 1, liquid inlets (18b, 18y) and liquid outlets (20b, 20y) are preferably positioned in a quiescent section below the respective gas inlets (12b, 12y) and spargers (14b, 14y), to allow liquid to be fed to, and withdrawn from, this section or reactor location of a given bioreactor stage. It is also possible, however, for inlets and outlets to be positioned elsewhere along the length of their respective bioreactors, depending on the desired locations for the feeding and withdrawal of liquid products. In an alternative embodiment, for example, liquid outlets may be positioned at or near the levels of gas/liquid interfaces (22a, 22b, 22y, 22z), or may otherwise disrupt the siphoning effect or liquid-full condition between bioreactor stages, in order to allow independent liquid level control in one or more bioreactors.

As also shown in FIG. 1, one or more, for example all, bioreactors (100a, 100b . . . 100y, 100z) may include external liquid recycle loops (25a, 25b . . . 25y, 25z) (i.e., external to their respective bioreactors) to improve mixing/uniformity within a given bioreactor and/or improve the rate of vapor-liquid mass transfer. Using external liquid recycle loops (25a, 25b . . . 25y, 25z), liquid product, including culture medium and C1-fixing microorganism, may be withdrawn from a bottom section of a given bioreactor (e.g., from within the bottom 10% of the length of the bioreactor; from below gas distribution devices, such as spargers (14a, 14b, 14y, or 14z); and/or from below the liquid inlets or liquid outlets) and recycled externally to the bioreactor, to a top section of the bioreactor (e.g., to within the top 10% of the bioreactor and/or to above gas/liquid interfaces (22a, 22b, 22y, or 22z) that demarcate boundaries between a continuous gas phase zone and a continuous liquid phase zone). External reactor liquid recycle loops may include respective, external liquid recycle pumps (30a, 30b, 30y, 30z) to provide the external liquid circulation at a desired rate, for example at an optimum tradeoff between energy usage and mass transfer rate improvement.

Conveniently, external liquid recycle loops (25a, 25b . . . 25y, 25z) can provide locations of bioreactor liquid sampling/analysis, and also be configured for bioreactor control. For example, bioreactors 100a and 100b of the first and second stages include respective external liquid recycle loops 25a and 25b, to which a basic neutralizing agent (e.g., an aqueous base such as $NH_4OH$ or NaOH) may be added through basic neutralizing agent inlets 35a and 35b. The addition of a basic neutralizing agent to given bioreactor(s), for example bioreactors 100a, 100b may be separately controlled using suitable feedback control loops, including, for example, pH analyzers 40a, 40b that measure (e.g., continuously or intermittently) the pH value of bioreactor liquid within external liquid recycle loops 25a and 25b. Such control loops also include the requisite hardware (e.g., control valves or variable rate feed pumps, not shown) and software (e.g., computer programs) for comparing the measured pH value to a set point value for a given bioreactor, and then controlling the flow of basic neutralizing agent to achieve or maintain the set point. Therefore, external recycle loops of one or more (e.g., all), of the bioreactors may be in fluid communication with respective, one or more (e.g., all), basic neutralizing inlets and comprise instrumentation for independently controlling pH within the one or more (e.g., all), respective bioreactors.

Also, external liquid recycle loops (25a, 25b . . . 25y, 25z) of one or more bioreactors (100a, 100b . . . 100y, 100z) may include temperature transmitters (41a, 41b, 41y, 41z) that measure (e.g., continuously or intermittently) the temperatures of liquid within external liquid recycle loops 25a and 25b of respective bioreactors (100a, 100b . . . 100y, 100z), such temperatures being representative of operating temperatures of the bioreactors. Separate bioreactor temperature control may therefore be achieved using control loops including, in addition to temperature transmitters (41a, 41b, 41y, 41z), heaters or heat exchangers (42a, 42b, 42y, 42z) and requisite software (e.g., computer programs) for comparing the measured temperature to a set point temperature for a given bioreactor, and then controlling the operation of heaters or heat exchangers (42a, 42b . . . 42y, 42z) to achieve or maintain the set point. Specific types of heat exchangers include those having tube-in-tube and dimple jacket constructions. Additionally, external liquid recycle loops (25a, 25b . . . 25y, 25z) of one or more bioreactors (e.g., bioreactors 100a and 100b of the first and second stages as depicted in FIG. 1) may include liquid culture medium inlets 45a and 45b, or inlets for introducing other liquid diluents, reagents (e.g., surfactants), and/or nutrients, to the one or more bioreactors independently at the same or varying rates. Therefore, external recycle loops of one or more (e.g., all), of the bioreactors may be in fluid communication with respective, one or more, heaters or heat exchangers and comprise instrumentation for independently controlling temperatures within the one or more, respective bioreactors.

Two or more of the bioreactor stages (e.g., first and second bioreactor stages 10a, 10b) may therefore have independently controllable process operating variables, including those that require sampling/analysis of bioreactor liquid product on the external liquid recycle loops, as described above. Representative process operating variables include liquid culture medium addition rate, gaseous CO-containing substrate feed rate, reactor temperature, reactor pH, and combinations thereof. One important advantage of multi-stage processes as described herein arises from the ability to independently control growth of the C1-fixing microorganism as it is transferred to successive bioreactor stages. Management of bacterial growth, as well as the production of the end product and other metabolites, can be accomplished by tailoring the conditions of a given bioreactor stage (e.g., the process operating variables described above) to a given processing objective. For example, according to one embodiment, a relatively high rate of liquid culture medium is added to the bioreactor of the first stage to promote a high bacterial growth rate and also set a stable homogeneous culture for the rest of the multi-stage bioreactor system. Comparatively lower rates of liquid culture medium can be added to downstream bioreactors, having more established cell cultures, suitable for achieving high production rates of the end product. In this manner, bacterial growth can be advantageously separated or decoupled from product generation. Overall, it can be appreciated more generally that the systems described herein offer a high number of degrees of freedom, in terms of controlling the metabolism of C1-fixing microorganism as it progresses through different phases of growth in each successive reactor. These control features allow the multi-stage biological conversion processes to be operated with a final stage liquid product having the characteristics as described above.

In the same manner, the liquid levels, or heights of gas/liquid interfaces ($22a$, $22b$ . . . $22y$, $22z$) may be independently controlled in one or more bioreactors ($100a$, $100b$ . . . $100y$, $100z$), through the use of separate liquid level control equipment and instrumentation (e.g., control valves, level sensors, and transmitters). However, it is also possible to avoid, advantageously, the added expense and complexity of implementing such equipment and instrumentation, by carrying out the multi-stage processes such that the liquid level in at least one bioreactor is dependent upon the liquid level in its respective, downstream bioreactor, for example by having a single level control that controls liquid levels in all bioreactors of the system. According to a particular mode of operating the system of bioreactors ($100a$, $100b$ . . . $100y$, $100z$) of FIG. 1, liquid culture medium is added to bioreactor $100a$ of the first stage through inlet $45a$ and flows through all reactors by overflow or otherwise as governed by the hydrostatic head, for example which can be controlled by varying the highest elevation E to which the final stage liquid product reaches or extends.

According to one possible procedure for initiating the process, the bioreactor $100a$ of the first stage may be inoculated or charged with C1-fixing microorganism initially, which, after a period of batch growth in culture, achieves a sufficiently high concentration, such that continuous addition of liquid culture medium can be initiated. The first stage liquid product is then conveyed to successive stages, for example by overflow from the first stage to the second stage, followed by overflow from the second stage to the third stage, etc. The liquid level of the system may ultimately be determined by the level at which the final stage liquid product is withdrawn (also referred to as the level of the "bleed" from the final bioreactor stage). Gaseous C1-containing substrate is added to each reactor separately, although a shared headspace, into which vapors exiting from continuous liquid phase zones are combined (e.g., in the case of more than one bioreactor stage being disposed within a single vessel, such as in a stacked arrangement) is possible, and, according to some embodiments, may reduce foaming. The desired end product of the fermentation, as well as other metabolites, are recovered from the final stage liquid product, withdrawn from the final bioreactor stage. The final stage liquid product may be separated (e.g., by membrane filtration) to remove the end product and metabolites, and then the C1-fixing microorganism and possibly other solids, prior to this recovery. Some or all of the liquid permeate that is recovered from this separation (or base medium) may be recycled for use in a bioreactor stage, for example, it may be added to the first stage bioreactor, optionally following the addition of nutrients.

Figure 2:
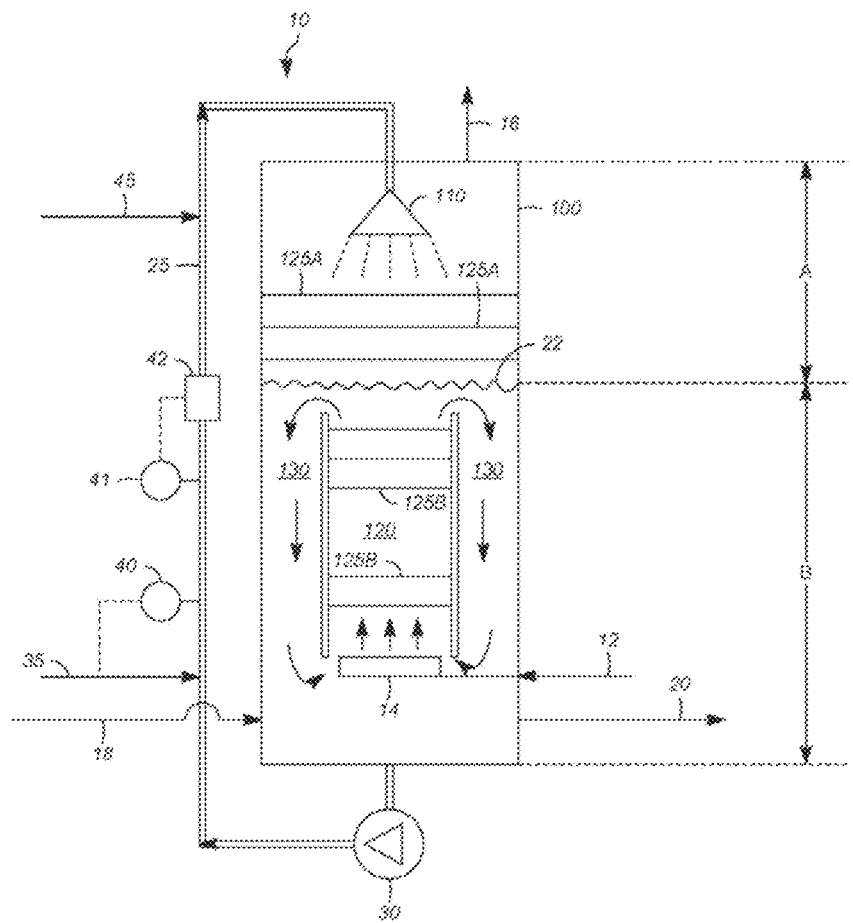
FIG. 2 depicts a close-up view of a representative bioreactor as shown in FIG. 1, and provides additional details relating to internal structures and liquid circulation.

FIG. 2 depicts one possible type of bioreactor $100$, namely a circulated loop bioreactor, which can be incorporated into a bioreactor stage $10$ of a multi-stage process, including the process depicted in FIG. 1. Many of the same features are as shown in FIG. 1 (and identified with the same reference numbers), with the exception of some of the reactor internal structures that may be used specifically to promote desired vapor and liquid flow characteristics, circulation, and distribution/mass transfer between the phases. As more clearly shown in FIG. 2, bioreactor $100$ operates with two zones that are distinguishable by their continuous and dispersed phases. Continuous vapor phase zone A has a dispersed liquid phase, by virtue of liquid product entering this zone (also referred to as the headspace) through one or more liquid distribution devices such as shower head $110$ having a plurality of openings for dispersing downwardly flowing liquid product (e.g., in a downwardly expanding cone profile), fed from external liquid recycle loop $25$.

Continuous liquid phase zone B has a dispersed gas phase, by virtue of C1-containing substrate entering this zone through one or more gas distribution devices, such as sparger $14$, having a plurality of openings for dispersing upwardly flowing C1-containing substrate, fed from gas inlet $12$. Gas/liquid interface $22$ demarcates the boundary between continuous gas phase zone A and continuous liquid phase zone B. Continuous liquid phase zone B may occupy a majority of the volume of bioreactor $100$, and, for example, it may be disposed entirely within the bottom 90%, the bottom 80%, or the bottom 75% of the reactor length. Accordingly, gas/liquid interface $22$ may be located within the top 25%, the top 20%, or the top 10% of the reactor length. In some cases, a layer of foam (not shown) may reside above gas/liquid interface, and, for purposes of this disclosure, resides in continuous gas phase zone A.

Therefore, according to the specific embodiment of FIG. 2, liquid product (or "broth") recycled through external liquid recycle loop $25$ is introduced to continuous vapor phase zone A. This liquid product may be passed from the bottom section of the bioreactor, from which the liquid product is withdrawn as described above, to a top section of the bioreactor (e.g., to within the top 10% of the length of bioreactor $100$ and to above liquid distribution device(s), such as shower head $110$, through which the liquid product is introduced). As described above with respect to FIG. 1, external liquid recycle loop $25$, in addition to improving liquid circulation and mass transfer between the liquid and vapor phases, can be configured to perform process control functions. For example, liquid product, recycled through external recycle loop $25$, may be passed through external heat exchanger $42$ (e.g., prior to being introduced continuous vapor phase zone A) for control of the temperature of bioreactor $100$. Otherwise, a basic neutralizing agent may be added to this liquid product, for example through basic neutralizing agent inlet 35, to control the pH of bioreactor 100. In the case of a plurality of bioreactors as shown in FIG. 1, external recycle loops of one or more (e.g., all), of the bioreactors may be used for recycling liquid product, withdrawn proximate one or more, respective, first ends of the bioreactors, to liquid distributors in one or more, respective continuous vapor phase zones proximate one or more, respective second ends (disposed opposite the first ends).

C1-containing substrate, introduced through sparger 14, may be fed to a riser 120 that is disposed within continuous liquid phase zone B, for example concentrically with respect to bioreactor 100, and confines rising gas bubbles to a central region of this zone. After exiting the top of riser 120, remaining gas, not dissolved or utilized in continuous liquid phase zone B, continues flowing upwardly and becomes disengaged from this zone at gas/liquid interface 22. Due to gas holdup in riser 120 the overall density within riser 120 is less than the density in downcomer 130, from which gas bubbles are substantially disengaged. As shown in FIG. 2, downcomer 130 may be disposed annularly with respect to riser 120 although other configurations are possible for providing regions within continuous liquid phase zone B of differing density. For example, a plurality of vertically extending downcomers may be distributed throughout this zone, extending from within bottom 1%-10% of the reactor length to within the top 25%-45% of the reactor length. As also shown using arrows in this zone to indicate the bulk liquid flow direction, bioreactor 100 operates with internal liquid circulation in continuous liquid phase zone B, which is namely induced by the differences in density, and results in upward liquid flow in riser 120 and downward liquid flow in downcomer 130, both being internal to bioreactor 100. According to some embodiments more than one riser and/or more than one downcomer may be used for control of the liquid circulation.

Gas that becomes disengaged at gas/liquid interface 22 continues flowing upwardly (in bulk) through continuous vapor phase zone A, where it is contacted with liquid product introduced into this zone through shower head 110 or other liquid distribution device. In this manner, bioreactor 100 operates with countercurrent gas and liquid flows (upwardly flowing gas and downwardly flowing liquid) in this zone, which is disposed above continuous liquid phase zone B, operating with internal liquid circulation as described above. Both of these zones may comprise vapor-liquid contacting devices. Due to differences in how mass transfer between phases is effected in these zones, vapor-liquid contacting devices 125A in zone A may differ from vapor-liquid contacting devices 125B in zone B, for example with respect to their geometry (e.g., diameter and/or thickness) and/or configuration of their openings (e.g., in terms of size, shape, spacing, and/or total number). According to some embodiments, completely different types of vapor-liquid contacting devices (e.g., perforated plates and random packing materials such as Raschig rings) may be used in the different zones. Likewise vapor-liquid contacting devices that differ, or that are of completely different types, may be used within a single zone.

As can be appreciated by those having skill in the art, having regard for the present specification, multi-stage processes and systems described herein are associated with a number of operational advantages, including any one, any combination, or all of the following, (1) robust fermentation (anaerobic bioconversion) with reduced complexity: Relative to conventional processes, multi-stage processes as described herein are simpler to operate and have a significantly greater "operating envelope" or range of conditions under which operation is feasible. This results from relatively low productivity requirements for each individual bioreactor, and the continuous feed that all reactors (other than the bioreactor of the first stage) receive from the immediately upstream reactor, stabilizing fermentation. This advantageously addresses one of the major objectives in this art, namely operational robustness at scale, as needed for long-term, stable commercial operation. (2) a significant number of degrees of freedom: This allows greater control of a bacterial culture's metabolism as it progresses through different phases of growth in each bioreactor. Conditions at each stage (e.g., gas supply rate, temperature, and/or pH set-point), can be tailored to control fermentation outputs, such as metabolite ratios. This can result in high and stable end product titers. For example, the inventors have demonstrate high and stable ethanol titers (>60 grams/liter in continuous laboratory testing), very favorable and stable final liquid product ethanol:acetate weight ratios (100+ in continuous laboratory testing). Accordingly, a potentially very large cost savings may be realized, relating to the use of culture media and water recycling systems, where the acetate byproduct is the main hindrance to direct recycle. (3) an ability to separate growth from product generation: This is a significant benefit for the production of biological end products from genetically engineered cells, in processes in which an inducer can be added at latter stages, after growth. Benefits result from the possibility of having a high growth rate in the first bioreactor stage, using a high dilution rate (i.e., rate of addition of liquid culture medium), which sets a stable homogenous culture for the remainder of the system. (4) a large savings in capital cost, without the requirement for a cell recycle system: In this regard, membranes, housings, valves and associated instruments and controls represent a significant portion of the total cost of the bioreactors, especially at commercial scale. Bacteria cell recycle requirements (e.g. the recycle pump duty) are also significantly reduced, and may require only the modest energy needed for operating external recycle loops (e.g., through a shower head or other liquid distributer as described above). (5) simplified and more robust operation, at reduced cost: This results because membrane separation and recycle of the separated cells are not required at each bioreactor stage. Costs associated with changing membranes and manual cleaning in place (CIP) are significant, in terms of operator time, CIP chemicals, and heating. In this regard, automatic CIP options have prohibitively high capital cost, enzyme solutions for cleaning cell recycle membranes are likewise expensive, and simple NaOH cleaning procedures are often ineffective. (6) Larger volume, shorter, and squatter airlift loop reactor designs: Such designs can be readily fulfilled by existing industry standard bulk tanks, fitted with internals. This results from lower productivity requirements for the bioreactors, and allows for the possibility of substantial cost savings in bioreactor fabrication. According to some embodiments, processes and systems as described herein can operate effectively on an airlift circulation effect alone, without the use of an external recycle or loop pump, and consequently also forgoing the associated, external recycle piping and equipment. Further reductions in capital expenditures on control valves and piping are possible, in embodiments utilizing simple overflow/liquid head level control between each stage. (7) The use of low operating pressures: This is an additional benefit of lower productivity requirements, for the individual bioreactors. On this point, high gas holdup limits the gas flow rate to a bioreactor, unless the gas is pressurized. The ability to reduce operating pressure has the effect of reducing compression costs.

The following examples are set forth as representative of the present invention. These examples are not to be construed as limiting the scope of the invention, as these and other equivalent embodiments will be apparent in view of the present disclosure and appended claims.

EXAMPLE 1

Experimental Setup

A test rig having six stages comprising bioreactors, each with a 1.5 liter working volume (for a total reactor volume of 9 liters for the system) was used for the extended evaluation of a multi-stage biological conversion process as described herein. Specifically, these processes used countercurrent, liquid downflow loop reactors having main columns of about 1.2 meters high and 50 millimeters in diameter and constructed of clear PVC plastic for observation of hydrodynamics. The fifth and sixth stages had somewhat taller main columns. A plastic, low pressure centrifugal pump (aquarium duty, 500-2000 L//h) at the bottom of each column was used to recycle liquid to a full-cone shower head liquid distributor at the top of the column. The pressure drop across each shower head was low, on the order of 20-40 kPa.

Gas entered each bioreactor stage separately and near the bottoms of the columns, through sintered stainless steel spargers. Un-utilized and undissolved gas exited at the top of each column, above the shower head. All six stages were run at nearly atmospheric pressure. Each stage was connected fluidly to the next (for the transfer of liquid products) by small bore stainless steel lines (1.5 mm inner diameter tubing), attached at the bottom of each main column, just below their respective spargers. Liquid culture medium was fed to the first stage, and was transferred through the system of bioreactor stages by liquid head alone. The final or sixth stage was used to control the reactor liquid levels in the whole system, using a liquid take-off point that was adjustable in elevation. Each stage was equipped with separate dosing chemical lines and temperature control. Apart from the final two stages (i.e., the fifth and sixth stages), the stages were also equipped with pH measurement and control systems.

EXAMPLE 2

Initial, Shakedown Operation

An initial operation was designed to test the effectiveness of a multi-stage bioreactor system for the biological conversion of CO in a gaseous CO-containing substrate to ethanol and other metabolites, in the presence of a bacterial culture medium containing *C. autoethanogenum*. A simplified version of the test rig as described in Example 1 was employed, without headspace shower sprays, i.e., the continuous vapor phase zone was an open pipe. Nor were any spargers used, i.e., gas was introduced into the continuous liquid phase zone through an open, 3 mm inner diameter tube. Temperature control on the bioreactors of the fifth and sixth stages was lacking, and liquid level control was maintained with a simple, overflow liquid system (shared gas outlet). The bioconversion operation achieved stable bacterial growth for 2 weeks, eventually reaching an operating point of >43 grams/liter of ethanol production with <2 grams/liter of acetate production, based on the final stage liquid product withdrawn from the bioreactor of the sixth stage. The steady-state dilution rate, or addition of liquid culture medium, was approximately 2.5 milliliters per minute (or about 2.3 reactor volumes per day for each bioreactor). These results validated the system for overflow liquid level control, although some mass-transfer generating surfactants were observed to be removed in the overhead liquid level from the initial bioreactor stages, reducing mass transfer.

EXAMPLE 3

Modified Operation, Based on Hydrodynamic Observations

In a second operation, modifications were made to arrive at the test rig substantially as described in Example 1. These modifications, based on hydrodynamic evaluation of the testing in Example 2, included establishing "liquid only" connections between the stages, using 1.5 mm inner diameter, stainless steel tubing attached at the bottoms of the columns. This diameter was determined to be sufficiently small to prevent back mixing at the operating rates of culture medium addition (dilution rates). In view of these liquid connections at the bottoms of the reactors, an adjustable height outlet for the final stage liquid product, exiting the sixth bioreactor, was added for liquid level control throughout the system. Also, full cone headspace shower sprays were added to all of the bioreactors for liquid distribution, and temperature control systems were added on the external liquid recycle loops of the final two reactor stages. Separate gas exhausts were provided for each of the six bioreactors, as opposed to having the gaseous products, containing un-utilized CO, combined as described in Example 2.

Figure 3:
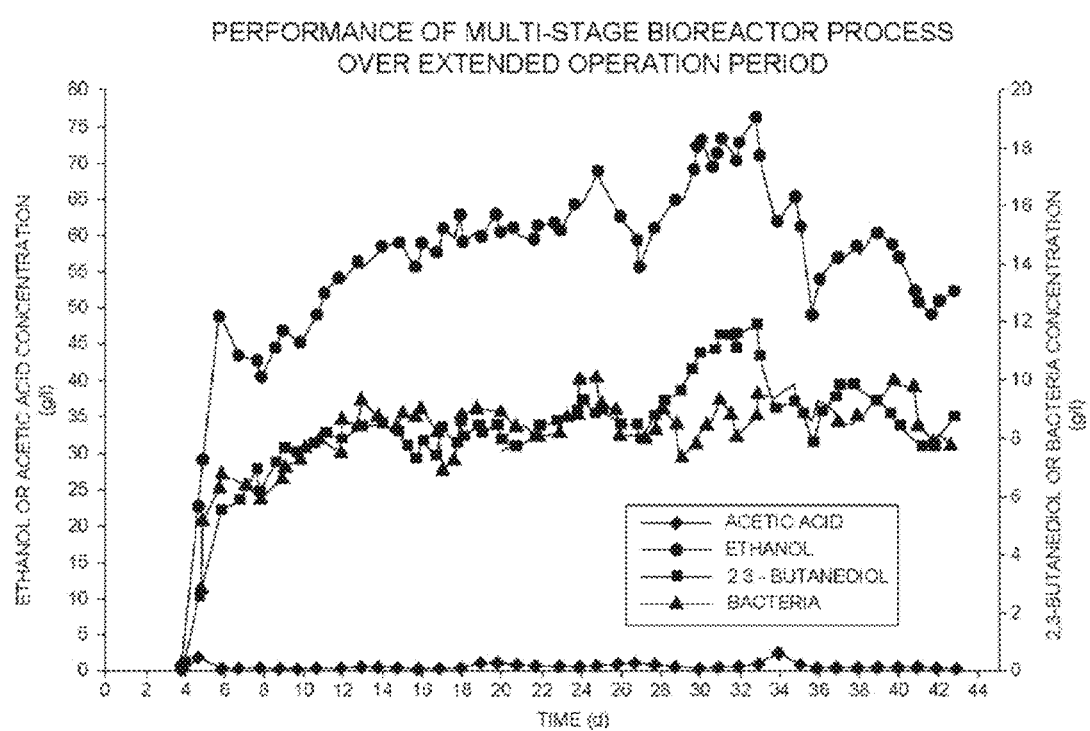
FIG. 3 is a graph showing concentrations of ethanol and carboxydotrophic microorganism, as well as the byproduct metabolites of acetic acid and 2,3-butanediol, over a 40+ day period of operation, in samples taken of the final liquid product of a biological process described herein, utilizing six bioreactor stages.
Figure 4:
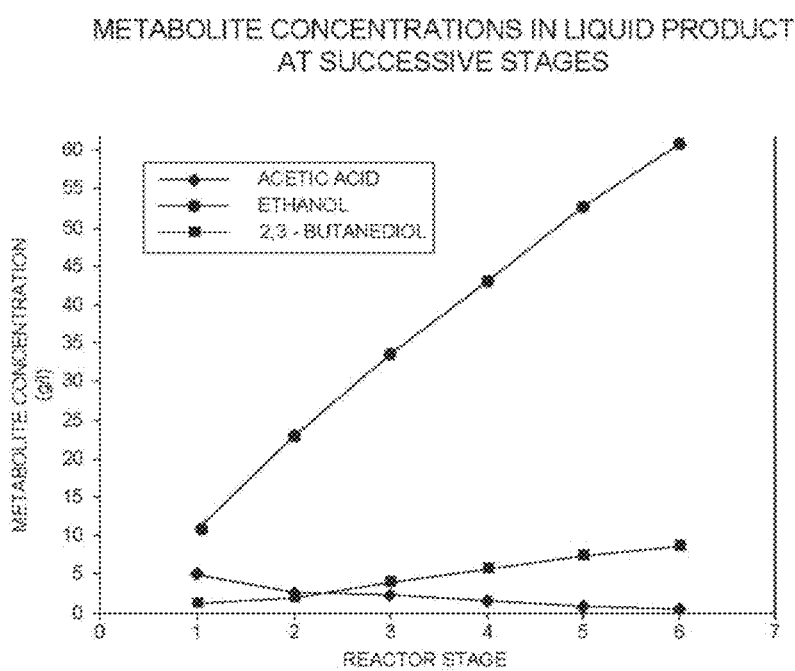
FIG. 4 a graph of measured concentrations of ethanol and the byproduct metabolites of acetic acid and 2,3-butanediol, in samples taken of liquid products from each of the six bioreactor stages, at day 23 of the 40+ day period of operation, for which the final liquid product concentrations are depicted in FIG. 3.

A 48-day test of the biological conversion reaction described in Example 2 was conducted with stable operation. Under continuous conditions, productivity and product quality were both very favorable. For example, over a 10-day period, steady-state operating parameters (e.g., pressures, temperatures, flow rates, pH values, etc.) achieved final stage liquid product ethanol titer averaging greater than 61 grams/liter and an acetate (acetic acid) titer averaging only 0.6 grams/liter (about a 100:1 w/w ratio or greater, of ethanol/acetic acid). The 2,3-butanediol titer averaged 8.4 grams/liter. These results were achieved with liquid culture medium addition of approximately 2.5 milliliters per minute (or a dilution rate of about 2.3 reactor volumes per day for each bioreactor). Importantly, over 33 days of continuous operation, ethanol titers were consistently above 50 grams/liter, with surprisingly high titers of above 70 grams/liter for 3 days, and even a peak titer of 76 grams/liter during the operation. When the culture medium addition rate to the second, third, and fourth bioreactor stages was increased, to obtain a dilution rate of 3.5 reactor volumes per day in the final bioreactor, over 50 grams/liter of ethanol was obtained in the final stage liquid product. The performance achieved over this extended operation is illustrated in FIG. 3, which provides the concentrations, in the final stage liquid product, of ethanol and other metabolites, namely acetic acid and 2,3-butanediol, as well as the microorganism (biomass) concentration. The metabolite profile (ethanol, acetic acid, and 2,3-butanediol concentrations) for the liquid products of each stage is illustrated in FIG. 4, based on liquid product samples taken at 23 days on stream. FIG. 4 shows, in particular, the rapidly increasing ethanol concentrations obtained at successive stages, and at the same time, only a very modest increase in the 2,3-butanediol concentration and a decrease in the acetate (acetic acid) concentration. Results from this operation included individual bioreactor stage CO utilizations of 65-75% during stable operation at the beginning of the 48-day test, which increased to 80-90% at later time periods when higher ethanol product titers were achieved. These results are indicative of very high mass transfer coefficients for column/loop reactors of this scale.

Advantageously, the high titers of the end product ethanol and the exceptionally stable operation were achieved, at least in part, through the positioning of the liquid transfer lines at the bottoms of the reactors and addition of the liquid distributors in the reactor headspaces. This had the effect of reducing some drawbacks related to foam buildup and preferential transfer of chemical additives out of the top of the liquid phase. Overall, both mass transfer and operational control were significantly improved, as a result of the modifications made between the tests conducted in Examples 2 and 3. In addition, the gas-liquid interface levels were consistently at the tops of their respective columns/reactors, and more easily controlled, regardless of the actual liquid inventory (real liquid volume). Therefore, the amount of holdup could be directly controlled by the liquid inventory, which, in the case of the multi-stage bioreactor system used in Example 3, was in turn regulated using an external drain line. This line, used to withdraw the final bioreactor stage liquid product, was connected to an adjustable height siphon breaker, allowing the liquid phase within the columns to be set to any desired level. Particularly good results were obtained with a liquid head height approximately extending to the top 30-50% of the reactor length (e.g., nominally 40% holdup).

Based on the results obtained in Examples 2 and 3, processes and systems as described herein have an exceptionally high potential for improving vapor-liquid mass transfer, with relatively low, or even no, requirements in terms of additional energy input and/or capital expenditures. Operation is simplified, and cost savings may be realized, for example, by foregoing expenses associated with at least some membrane separation systems and/or level control systems (and associated flowmeters, pumps, control valves, and other instrumentation and equipment.

Overall, aspects of the invention are directed to multi-stage bioreactor processes, utilizing particular vapor and liquid flow configurations as described above, which lead to a number of process advantages, particularly with respect to achieving high productivity of the desired end product, coupled with simplicity of fabrication of the associated systems. Those having skill in the art, with the knowledge gained from the present disclosure, will recognize that various changes can be made, without departing from the scope of the present invention.

The invention claimed is:

1. A multi-stage process for converting C1 carbon source into an end product, the process comprising:
feeding a gaseous C1-containing substrate, in parallel, to a first bioreactor stage and at least a second bioreactor stage of the multi-stage process,
feeding at least a portion of a first stage liquid product, in series, from the first bioreactor stage to the second bioreactor stage,
wherein the first stage liquid product comprises a C1-fixing microorganism used in the first bioreactor stage to metabolize C1-carbon source and generate the end product.

2. The process of claim 1, wherein the first stage liquid product is fed to the second bioreactor stage, without separation of the C1-fixing microorganism and recycle of separated C1-fixing microorganism to the first bioreactor stage.

3. The process of claim 1, comprising at least four bioreactor stages in which the gaseous C1-containing substrate is fed in parallel to the stages, and liquid products, including the first stage liquid product, are fed successively from the first bioreactor stage to a final bioreactor stage, and then withdrawn from the final bioreactor stage.

4. The process of claim 3, wherein an overall C1 utilization of the at least four bioreactor stages is at least about 60%.

5. The process of claim 3, wherein the at least four bioreactor stages are operated at a pressure of less than about 200 kilopascal (kPa) above atmospheric pressure.

6. The process of claim 1, wherein the end product is ethanol and, in addition to ethanol, the C1-fixing microorganism generates acetic acid as a metabolite.

7. The process of claim 6, further comprising withdrawing a final stage liquid product from a final bioreactor stage of the multi-stage process, wherein a biomass free liquid fraction of the final stage liquid product comprises at least about 50 grams per liter (g/l) of ethanol.

8. The process of claim 7, wherein the biomass free liquid fraction of the final stage liquid product has an ethanol: acetic acid weight ratio of at least about 50:1.

9. The process of claim 1, wherein the end product is a growth dependent product selected from the group consisting of isopropanol, butanol, acetate, acetone, 2-hydroxyisobutyric acid and isobutylene.

10. The process of claim 9, further comprising withdrawing a final stage liquid product from a final bioreactor stage of the multi-stage process, wherein a biomass free liquid fraction of the final stage liquid product comprises at least about 10 grams per liter (g/l) of isopropanol.

11. The process of claim 1, wherein the first and second bioreactor stages have at least one independently controllable process operating variable selected from the group consisting of liquid culture medium addition rate, gaseous C1-containing substrate feed rate, reactor temperature, reactor pH, and combinations thereof.

12. The process of claim 1, wherein at least one of the first and second bioreactor stages comprises a bioreactor having a ratio of its length to its width of less than about 10:1.

13. The process of claim 1, wherein at least one of the first and second bioreactor stages comprises a circulated loop bioreactor.

14. The process of claim 13, wherein the circulated loop bioreactor operates with internal liquid circulation in a continuous liquid phase zone.

15. The process of claim 14, wherein, in the continuous liquid phase zone, liquid flows upward in an internal riser and downward in one or more internal downcomers.

16. The process of claim 14, wherein the circulated loop bioreactor operates with countercurrent gas and liquid flows in a continuous vapor phase zone, above the continuous liquid phase zone.

17. The process of claim 16, wherein the continuous liquid phase zone is within a bottom 75% of the length of the circulated loop bioreactor.

18. The process of claim 16, wherein the continuous liquid phase zone and continuous gas phase zone comprise vapor-liquid contacting devices, wherein continuous liquid phase zone devices differ from continuous vapor phase zone devices.

19. The process of claim 16, wherein liquid product, recycled through an external recycle loop, is to the continuous vapor phase zone.

20. The process of claim 19, wherein the liquid product that is recycled through the external recycle loop, is passed through an external heat exchanger for control of the temperature of the circulated loop bioreactor.

21. The process of claim 19, wherein a basic neutralizing agent is added to the liquid product that is recycled through the external recycle loop, to control the pH of the circulated loop bioreactor.

22. A multi-stage, biological process for converting CO to ethanol, the process comprising:
- dividing a gaseous CO-containing substrate, in parallel, among a plurality of bioreactor stages of the multi-stage process;
- successively feeding liquid products comprising carboxydotrophic microorganism, in series, from a first bioreactor stage to downstream bioreactor stages,
- withdrawing, from a final bioreactor stage, a final stage liquid product having a non-carboxydotrophic microorganism containing liquid fraction comprising at least about 50 grams per liter (g/l) of ethanol and having an ethanol : acetic acid weight ratio of at least about 50:1.

23. The process of claim 22, comprising at least four bioreactor stages.

24. The process of claim 22, wherein two or more of the plurality of bioreactor stages are separate sections within a single vessel.

* * * * *